United States Patent [19]

Prugh

[11] 4,212,871
[45] Jul. 15, 1980

[54] APPETITE STIMULATING AND ANTIHISTAMINIC 3-HYDROXYMETHYLCYPROHEPTADINE AND ANALOGS

[75] Inventor: John D. Prugh, Chalfont, Pa.
[73] Assignee: Merck & Co., Inc., Rahway, N.J.
[21] Appl. No.: 16,771
[22] Filed: Mar. 2, 1979
[51] Int. Cl.$^2$ ............... A61K 31/445; C07D 211/70
[52] U.S. Cl. ......................... 424/267; 546/203
[58] Field of Search ..................... 546/203; 424/267

[56] References Cited

U.S. PATENT DOCUMENTS

| | | | |
|---|---|---|---|
| 3,014,911 | 12/1961 | Engelhardt | 546/203 |
| 3,960,872 | 6/1976 | Prugh | 424/267 |
| 3,981,877 | 9/1976 | Prugh | 424/267 |

FOREIGN PATENT DOCUMENTS 1486847  9/1977  United Kingdom ................. 424/267

OTHER PUBLICATIONS

House, H., Modern Synthetic Reactions, W. A. Benjamin, New York, 1965, p. 34.

Primary Examiner—Henry R. Jiles
Assistant Examiner—Richard A. Schwartz
Attorney, Agent, or Firm—William H. Nicholson; Mario A. Monaco

[57] ABSTRACT

3-Hydroxymethyl derivatives of cyproheptadine and related compounds are appetite stimulants and antihistaminic agents.

8 Claims, No Drawings

APPETITE STIMULATING AND ANTIHISTAMINIC 3-HYDROXYMETHYLCYPROHEPTADINE AND ANALOGS

BACKGROUND OF THE INVENTION

This invention is concerned with 3-hydroxymethyl derivatives of cyproheptadine and related compounds which are appetite stimulants and antihistaminic agents.

Cyproheptadine itself and certain derivatives and analogs are known to be orexigenic and antihistaminic agents such as 3-carboxycyproheptadine in U.S. Pat. No. 3,981,877, 3-carboxy-10,11-dihydrocyproheptadine in British Pat. No. 1,486,847, 10-oxo (or hydroxy)-10,11-dihydrocyproheptadine in U.S. Pat. No. 3,960,872.

Now with this invention there are provided further novel cyproheptadine derivatives and analogs carrying a 3-hydroxymethyl group and novel processes for their preparation.

There is also provided a novel method of stimulating appetite and/or producing an antihistamine effect in patients in need of such treatment by the administration of one or more of the novel compounds or novel pharmaceutical compositions thereof which are also provided by this invention.

DETAILED DESCRIPTION OF THE INVENTION

The novel compounds of this invention have structural formula:

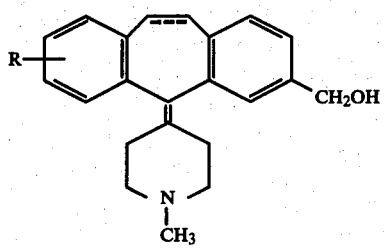

or a pharmaceutically acceptable salt thereof, wherein

R represents hydrogen, $C_{1-3}$ alkyl such as methyl, ethyl, propyl, especially methyl, or fluoro; and the dotted line represents saturation or unsaturation of the molecule at the 10,11-position.

It is preferred that R be hydrogen.

The novel compounds of this invention with a 10,11-double bond demonstrate atropisomerism and exist as dextro- and levorotatory enantiomers.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, pamoate, citrate, napsylate, pyruvate, isethionate, maleate, fumarate, or the like.

The salts are prepared by dissolving approximately equimolecular amounts of the free base compound and the desired acid in a solvent followed by crystallization of the salt product.

The novel process of this invention comprises reduction of the corresponding $C_{1-3}$-alkoxy carbonyl compound to a 3-hydroxymethyl. It is preferred that the reduction be conducted in an ethereal solvent such as tetrahydrofuran, tetrahydropyran, 1,2-dimethoxyethane or a di(lower alkyl) ether such as diethyl ether with a complex metal hydride as reducing agent such as lithium aluminum hydride. Other useful reducing agents are hydrogen in the presence of a copper chromium oxide catalyst at hydrogen pressures of 1–2 atmospheres and ambient temperature for 2–10 hours; and sodium in a $C_{2-6}$ alkanol such as ethanol or n-pentanol at about 20° C. to about reflux temperature until evolution of hydrogen ceases.

In the method of treatment and pharmaceutical composition aspects of the present invention it is noted that the precise unit dosage form and dosage level depend upon the case history of the individual being treated and consequently are left to the discretion of the therapist. In general, however, the compounds of the present invention produce the desired effect of appetite stimulation when given at from about 0.01 to about 10.0 mg per kg body weight per day. The preferred form of delivery of the instant compounds for appetite stimulation of domestic animals is by solution in drinking water or performulated feedstuffs. For human and animal administration, any of the usual pharmaceutical oral forms may be employed such as tablets, elixirs and aqueous suspensions comprising from about 0.01 to about 10.0 mg of the compounds of this invention per kg body weight given daily. Thus, for example, tablets given 2–4 times per day comprising from about 0.5 to about 50 mg of the compounds of this invention are suitable for human treatment. Sterile solutions (representatively given for human treatment) for injection comprising from about 0.1 to about 10.0 mg of the compounds of this invention given two to four times daily are also suitable means of delivery. When an antihistaminic effect is indicated, the above-recited dosage forms and levels are also appropriate.

EXAMPLE 1

1-Methyl-4-(10,11-dihydro-3-hydroxymethyl-5H-dibenzo[a,d]cyclohepten-5-ylidene)piperidine Step A:

Preparation of 1-methyl-4-(10,11-dihydro-3-ethoxycarbonyl-5H-dibenzo[a,d]cyclohepten-5-ylidene)-piperidine A solution of 5.0 g 1-methyl-4-(3-carboxy-10,11-dihydro-5H-dibenzo[a,d]cyclohepten-5-ylidene) piperidine hydrochloride in 200 ml of absolute ethanol was treated with 5 ml of boron trifluoride etherate. After stirring and refluxing for 18 hours the ethanol was evaporated in vacuo and the residue was partitioned between saturated aqueous sodium carbonate solution and ether. The ether phase was separated, washed with 3×100 ml of water, dried over anhydrous magnesium sulfate, filtered and evaporated to dryness. The residue, 5.4 g of 1-methyl-4-(10,11-dihydro-3-ethoxycarbonyl-5H-dibenzo[a,d]cyclohepten-5-ylidene)piperidine, after recrystallization from acetonitrile had m.p. 85°–87° C.

Step B:

Preparation of 1-methyl-4-(10,11-dihydro-3-hydroxymethyl-5H-dibenzo[a,d]cyclohepten-5-ylidene)piperidine A solution of 5.3 g of the ethyl ester from Step A in 200 ml of ether was added dropwise over about 30 minutes to a stirred mixture of 0.53 g of $LiAlH_4$ and 50 ml of ether. After the addition was complete the mixture was stirred 1 hour at ambient temperature, warmed to reflux and allowed to cool spontaneously to ambient temperature. With vigorous stirring a saturated aqueous solution of ammonium chloride was added slowly until a granular precipitate and a clear ether phase formed. Anhydrous magnesium sulfate was added. After stirring a short time the mixture was filtered and the filtrate was concentrated to dryness to give 2.28 g of 1-methyl-4-(10,11-dihydro-3-hydroxymethyl-5H-dibenzo[a,d]-cyclohepten-5-ylidene)piperidine, m.p. 178°–181° C. after recrystallization from acetonitrile.

Employing the procedure substantially as described in Example 1 but substituting for the 1-methyl-4-(3-carboxy-10,11-dihydro-5H-dibenzo[a,d]-cyclohepten-5-ylidene)piperidine used in Step A thereof an equimolecular amount of 1-methyl-4-(3-carboxy-5H-dibenzo[a,d]cyclohepten-5-ylidene) piperidine, there is produced 1-methyl-4-(3-hydroxymethyl-5H-dibenzo[a,d]cyclohepten-5-ylidene)piperidine, m.p. 174°–176° C.

Similarly prepared are:

1-methyl-4-(10,11-dihydro-3-hydroxymethyl-7-methyl-5H-dibenzo[a,d]cyclohepten-5-ylidene)piperidine;

1-methyl-4-(3-hydroxymethyl-7-methyl-5H-dibenzo-[a,d]cyclohepten-5-ylidene)piperidine;

1-methyl-4-(10,11-dihydro-7-fluoro-3hydroxymethyl-5H-dibenzo[a,d]cyclohepten-5-ylidene)-piperidine; and 1-methyl-4-(7-fluoro-3-hydroxymethyl-5H-dibenzo-[a,d]cyclohepten-5-ylidene)piperidine.

EXAMPLE 2

Pharmaceutical Compositions

A typical tablet containing 1 mg 1-methyl-4-(3-hydroxymethyl-10,11-dihydro-5H-dibenzo[a,d]cyclohepten-5-ylidene)piperidine per tablet is prepared by mixing together with the active ingredient calcium phosphate, lactose and starch in the amounts shown in the tablets below. After these ingredients are thoroughly mixed, the appropriate amount of magnesium stearate is added and the dry mixture blended for an additional three minutes. This mixture is then compressed into tablets weighing approximately 124 mg each.

| TABLE FORMULA | |
|---|---|
| INGREDIENT | MG. PER TABLET |
| 1-Methyl-4-(10,11-dihydro-3-hydroxymethyl-5H-dibenzo-[a,d]cyclohepten-5-ylidene)-piperidine | 1 mg |
| Calcium phosphate | 52 mg |
| Lactose | 60 mg |
| Starch | 10 mg |
| Magnesium stearate | 1 mg |

What is claimed is:

1. A compound of structural formula:

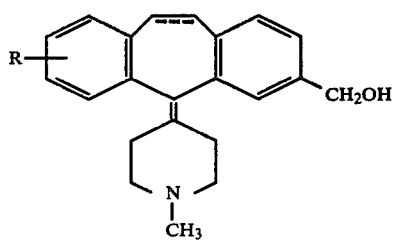

or a pharmaceutically acceptable salt thereof, wherein R is hydrogen, $C_{1-3}$ alkyl or fluoro, and the dotted line represents saturation or unsaturation.

2. The compound of claim 1, which is 1-methyl-4-(3-hydroxymethyl-5H-dibenzo[a,d]cyclohepten-5-ylidene)piperidine or 1-methyl-4-(10,11-dihydro-3-hydroxymethyl-5H-dibenzo[a,d]cyclohepten5-ylidene)-piperidine or pharmaceutically acceptable salts thereof.

3. A appetite stimulating or antihistaminic composition comprising a pharmaceutical carrier and respectively an appetite stimulating or antihistaminic amount of a compound of structural formula:

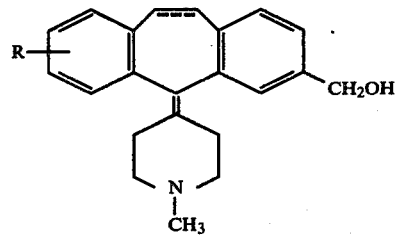

or a pharmaceutically acceptable salt thereof, wherein R is hydrogen, $C_{1-3}$ alkyl or fluoro, and the dotted line represents saturation or unsaturation.

4. The pharmaceutical composition of claim 3, wherein the compound is 1-methyl-4-(3-hydroxymethyl-5H-dibenzo[a,d]cyclohepten-5-ylidene)piperidine or 1-methyl-4-(10,11-dihydro-3-hydroxymethyl-5H-dibenzo[a,d]cyclohepten-5-ylidene)piperidine or pharmaceutically acceptable salts thereof.

5. A method of producing appetite stimulation comprising the administration to a patient in need of such treatment of an appetite stimulating amount of a compound of structural formula:

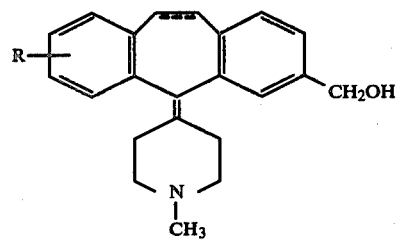

or a pharmaceutically acceptable salt thereof, wherein R is hydrogen, $C_{1-3}$ alkyl or fluoro, and the dotted line represents saturation or unsaturation.

6. The method of claim 5, wherein the compound is 1-methyl-4-(3-hydroxymethyl-5H-dibenzo-[a,d]cyclohepten-5-ylidene)piperidine or 1-methyl-4-(10,11-dihydro-3-hydroxymethyl-5H-dibenzo[a,d]cyclohepten-5-ylidene)piperidine or pharmaceutically acceptable salts thereof.

7. A method of producing an antihistaminic effect comprising the administration to a patient in need of such treatment of an antihistaminic amount of a compound of structural formula:

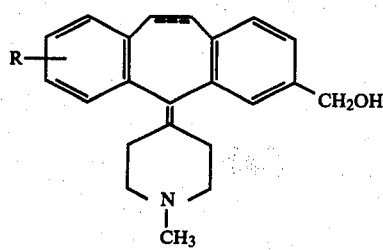

or a pharmaceutically acceptable salt thereof, wherein R is hydrogen, $C_{1-3}$ alkyl or fluoro, and the dotted line represents saturation or unsaturation.

8. The method of claim 7, wherein the compound is 1-methyl-4-(3-hydroxymethyl-5H-dibenzo-[a,d]cyclohepten-5-ylidene)piperidine or 1-methyl-4-(10,11-dihydro-3-hydroxymethyl-5H-dibenzo[a,d]-cyclohepten-5-ylidene)piperidine or pharmaceutically acceptable salts thereof.

* * * * *